United States Patent [19]

Buchanan

[11] Patent Number: 4,747,823
[45] Date of Patent: May 31, 1988

[54] CANNULAE

[76] Inventor: John M. Buchanan, Rowan House, Whitmore Heath, Near Newcastle, Staffordshire, England

[21] Appl. No.: 875,795

[22] Filed: Jun. 18, 1986

[30] Foreign Application Priority Data

Jul. 30, 1985 [GB] United Kingdom ............... 8519173

[51] Int. Cl.⁴ ............................................ A61M 25/00
[52] U.S. Cl. ...................................... 604/49; 604/104; 604/171; 604/282
[58] Field of Search ............... 604/282, 104, 171, 172, 604/178, 280, 49

[56] References Cited

U.S. PATENT DOCUMENTS

| | | |
|---|---|---|
| 3,680,562 | 8/1972 | Wittes et al. |
| 3,721,229 | 3/1973 | Panzer ............................ 604/174 X |
| 3,918,456 | 11/1975 | Patel ................................... 604/104 |
| 4,489,732 | 12/1984 | Hasson ................................ 128/778 |

FOREIGN PATENT DOCUMENTS

| | | |
|---|---|---|
| 0127781 | 12/1984 | European Pat. Off. |
| 322426 | 12/1929 | United Kingdom . |
| 1131865 | 10/1968 | United Kingdom . |
| 1218597 | 1/1971 | United Kingdom . |
| 1238086 | 7/1971 | United Kingdom . |
| 1297746 | 11/1972 | United Kingdom . |
| 1323375 | 7/1973 | United Kingdom . |
| 1347340 | 2/1974 | United Kingdom . |
| 1352483 | 5/1974 | United Kingdom . |
| 1434507 | 5/1976 | United Kingdom . |

Primary Examiner—Stephen C. Pellegrino
Attorney, Agent, or Firm—Pollock, Vande Sande and Priddy

[57] ABSTRACT

A cholangiogram cannula of flexible plastics has an enlarged olive close to its patient end. A transparent sleeve of polyethylene is a close sliding fit along the cannula between the olive and a connector at the machine end of the cannula. The cannula is graduated along its length, the graduations being visible through the sleeve. In use, the sleeve is slid forwards against the olive to provide a reinforced gripping site by which the cannula can be gripped between finger and thumb or by forceps. The patient end of the cannula is manipulated into an incision made in the cystic duct and the sleeve is then slid rearwardly and the cystic duct sealed about the cannula to the rear of the olive.

9 Claims, 2 Drawing Sheets

CANNULAE

BACKGROUND OF THE INVENTION

This invention relates to cannulae.

The invention is more particularly concerned with operative cholangiogram or similar cannulae.

Operative cholangiogram cannulae are used to introduce an X-ray opaque fluid into the common bile duct following removal of the gall bladder (cholecystectomy). This makes it possible to check, by X-ray observation, whether any small stones remain in the bile duct.

These cannulae are made of a plastics material, such as polyethylene, and are of a relatively small external diameter, typically about 1.4 mm. They are introduced into the bile duct using forceps to grip the end of the cannula.

One problem that arises with such cannulae is that they are easily crushed or kinked during introduction.

SUMMARY OF THE INVENTION

It is an object of the present invention to provide a cannula by which this problem can be alleviated.

According to one aspect of the present invention there is provided a flexible cannula that is arranged to open in the region of its forward, patient end, the cannula including a portion of enlarged cross section towards its patient end and a sleeve member mounted on the cannula to the rear of the portion of enlarged cross section, the sleeve member being shorter than the cannula and slidable along the cannula as far as the portion of enlarged cross section such that the cannula can be gripped on the sleeve member when it is close to the forward end of the cannula and the sleeve member subsequently slid rearwardly away from the portion of enlarged cross section.

The sleeve member is preferably a close sliding fit along the cannula. The rear, machine end of the cannula may be provided with a connector that is arranged to limit rearward displacement of the sleeve member along the cannula. The cannula may be of polyethylene. The sleeve member may be of a plastics such as polyethylene. The cannula may be graduated along its length and the sleeve member may be transparent so that the graduations are visible through the sleeve. The cannula may be a cholangiogram cannula the forward, patient end of the cannula being adapted for insertion in the cystic duct and the portion of enlarged cross section being adapted to prevent withdrawal of the cannula from the cystic duct when the cystic duct is secured to the cannula to the rear of the portion of enlarged cross section.

A cholangiogram cannula and a method of using the cannula in accordance with the present invention, will now be described, by way of example, with reference to the accompanying drawings.

DETAILED DESCRIPTION

Figure 1:
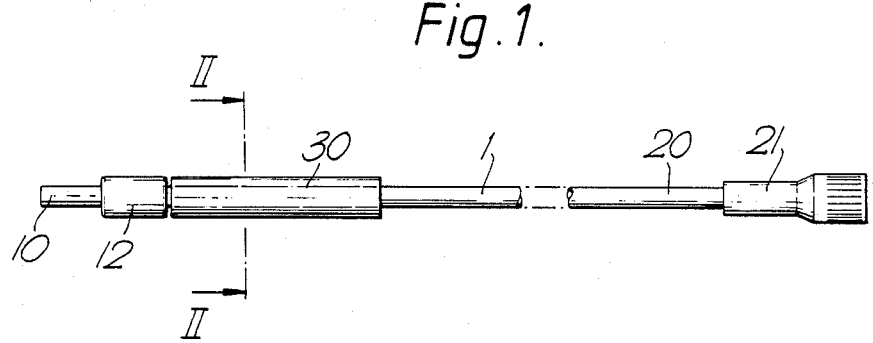
FIG. 1 is a side elevation of the cannula.
Figure 2:
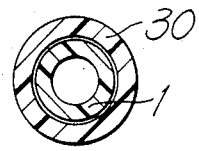
FIG. 2 is a transverse cross-section through the cannula of FIG. 1 along the line II—II, to an enlarged scale.

With reference to FIGS. 1 and 2, the cholangiogram cannula comprises a flexible polyethylene tube, or tubular member 1 of 1.4 mm external diameter and 1.1 mm internal diameter.

The forward, patient end 10 of the tube 1 is open and may be square as shown, or bevelled to form a sharp inclined tip. About 4 mm to the rear of the patient end 10 the cannula is provided with an integral olive 12 of generally cylindrical shape, being about 2.5 mm in diameter and about 5 mm in length. In general, portions of enlarged cross section with different shapes could be used.

At its rear end 20, the cannula has a female luer connector 21, the overall length of the cannula being about 610 mm.

The cannula so far described is conventional.

The novelty of the present cannula resides in the provision of a sleeve 30 which is slidable along the cannula. The sleeve 30 is about 100 mm long, of polyethylene, having an external diameter substantially the same as that of the olive 12. The internal diameter of the sleeve 30 is about the same as the external diameter of the tube 1, so that the sleeve 30 is a close sliding fit on the tube. As such, the sleeve 30 can be readily displaced along the tube 1 but remains in position at any point along the tube until displaced by the surgeon. Forward displacement of the sleeve 30 along the cannula is limited by engagement of the forward end of the sleeve with the olive 12, while rearward displacement is limited by engagement of the rear end of the sleeve with the connector 21.

Figure 3:
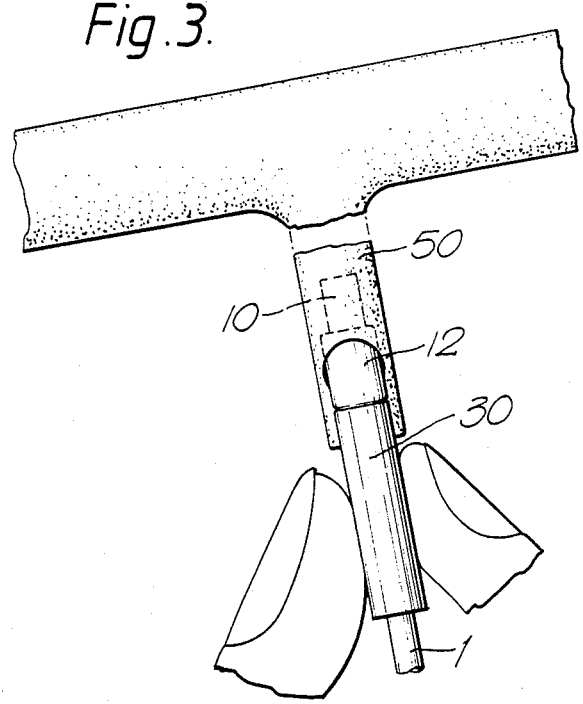
FIGS. 3 and 4 show the cannula in use.
Figure 4:
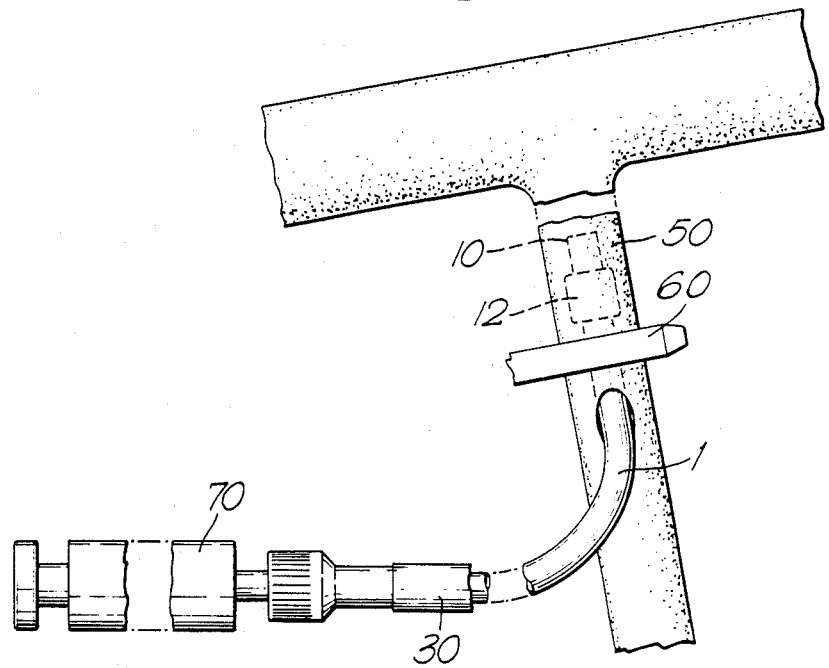

In use, the sleeve 30 is slid against the olive 12. The increased thickness and stiffness of the forward end of the cannula provided by the sleeve enables the forward end of the cannula to be gripped by the surgeon between fingers and thumb and manipulated into a small incision made in the cystic duct 50 as shown in FIG. 3. Alternatively, a pair of standard forceps may be used to grip the cannula, the jaws of the forceps being clamped about the sleeve 30 which provides a reinforced gripping site. The thickness of the wall of the sleeve 30 and the nature of the material from which it is made are such that when the sleeve is gripped it can be compressed slightly about the cannula to increase the friction between the sleeve and the cannula. The cannula is preferably graduated so that the length of cannula inserted can be readily determined, the sleeve 30 preferably being transparent so that the gradulations are visible through it. When correctly located, the sleeve 30 is slid to the rear end of the cannula. The crystic duct 50 is than sealed behind the olive 12 by clamping it with forceps 60, as shown in FIG. 4, or by means of a ligature. A radio-opaque fluid is then introduced to the duct from a syringe 70 while X-ray observation is made of the region in the usual way.

The sleeve 30 prevents the tube 1 being pinched closed and also stiffens the forward end of the cannula during introduction, thereby making manipulation easier and reducing the risk that the tube will become kinked.

Figure 5:
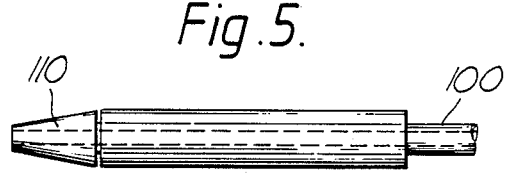
FIG. 5 is a side elevation of the tip of an alternative form of cannula.

In an alternative arrangement, shown in FIG. 5, the forward end of the cannula has a tapering, frusto-conical tip 110, the rear end of which is larger in diameter than the tube 100 so as to serve the same purpose as the olive 12 in the previous arrangement described above.

What I claim is:

1. A cholangiogram cannula comprising: a flexible, tubular member having a forward, patient end shaped for insertion into the cystic duct, and a rear, machine end, said tubular member being open in the region of said patient end and said tubular member having a portion of enlarged circular cross section fixed on said tubular member towards said patient end, said enlarged portion being shaped to prevent withdrawal of the cannula from the cystic duct when the cystic duct is secured to the cannula to the rear of said enlarged portion; and a sleeve mounted on the tubular member to the rear of said enlarged portion, said sleeve being of substantially cylindrical shape and circular cross section, shorter than the tubular member, being of substantially the same external diameter as that of said enlarged portion along at least the forward end of the sleeve, and being slidable along said tubular member as far as the rear of said enlarged portion to form a continuation of the surface of the enlarged portion such that the cannula can be gripped on the sleeve when it abuts said enlarged portion thereby to enable the cannula to be manipulated into the cystic duct and the enlarged portion to be pushed fully by said sleeve into the cystic duct.

2. A cannula according to claim 1, wherein said sleeve is a close sliding fit along the tubular member.

3. A cannula according to claim 1, wherein the said machine end of the cannula is provided with a connector, and wherein said connector limits rearward displacement of the sleeve along the cannula.

4. A cannula according to claim 1, wherein the said tubular member is of polyethylene.

5. A cannula according to claim 1, wherein the sleeve is of a plastics material.

6. A cannula according to claim 5, wherein the sleeve is of polyethylene.

7. A cannula according to claim 1, wherein the cannula is graduated along its length, and wherein the said sleeve is transparent so that the graduations are thereby visible through the sleeve.

8. A cholangiogram cannula comprising: a flexible, tubular member of plastics material, said tubular member having a forward, patient end shaped for insertion into the cystic duct, said patient end being open, and a rear, machine end, said machine end being open and provided with a connector, and said tubular member having a portion of enlarged circular cross section fixed on said tubular member towards said patient end, said enlarged portion being shaped to prevent withdrawal of the cannula from the cystic duct when the cystic duct is secured to the cannula to the rear of said enlarged portion; and a sleeve of plastics material mounted on the tubular member to the rear of said enlarged portion, said sleeve being of substantially cylindrical shape and circular cross section, being shorter than the tubular member, having substantially the same external diameter as that of said enlarged portion along at least the forward end of the sleeve, and being slidable along said tubular member as a close sliding fit between said portion of enlarged cross section and said connector such that the sleeve forms a continuation of the surface of the enlarged portion and such that the cannula can be gripped on the sleeve when it abuts said enlarged portion, thereby enabling the cannula to be manipulated into the cystic duct and the enlarged portion to be pushed fully by said sleeve into the cystic duct and the sleeve subsequently slid rearwardly away from the portion of enlarged cross section.

9. A method of introducing a cholangiogram cannula into a cystic duct comprising the steps of: providing a cholangiogram cannula having a flexible tubular member than opens in the region of its forward, patient end shaped for insertion into the cystic duct, and said tubular member having a portion of enlarged circular cross section fixed on said tubular member towards said patient end, the cannula including a substantially cylindrical sleeve of circular cross section mounted on the cannula to the rear of the portion of enlarged cross section, said sleeve being shorter than the tubular member, having substantially the same external diameter as that of said enlarged portion along at least the forward end of the sleeve, and being slidable along said tubular member as far as the rear of said portion of enlarged cross section; sliding said sleeve forwardly along the cannula into abutment with the portion of enlarged cross section so that the sleeve forms a continuation of the surface of the enlarged portion; gripping the cannula by the sleeve; manipulating the forward end of the cannula and the enlarged portion fully into the cystic duct while the cannula is so gripped by the sleeve; thereafter sliding the sleeve rearwardly away from the portion of enlarged cross section; and then securing the cystic duct about the cannula to the rear of the portion of enlarged cross section, said enlarged portion being shaped to prevent withdrawal of the cannula from the cystic duct after completion of said securing step.

* * * * *